(12) United States Patent
Hao et al.

(10) Patent No.: US 11,041,383 B2
(45) Date of Patent: Jun. 22, 2021

(54) SYSTEM AND METHOD FOR SCANNING WHILE-DRILLING ROCK FRAGMENTS IN AN OIL AND GAS FIELD

(71) Applicant: INSTITUTE OF GEOLOGY AND GEOPHYSICS, CHINESE ACADEMY OF SCIENCES, Beijing (CN)

(72) Inventors: Jin Hao, Beijing (CN); Jijin Yang, Beijing (CN); Jianguo Wu, Beijing (CN); Guoliang Li, Beijing (CN); Zhongming Du, Beijing (CN); Yuan Yuan, Beijing (CN)

(73) Assignee: INSTITUTE OF GEOLOGY AND GEOPHYSICS, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 16/741,699

(22) Filed: Jan. 13, 2020

(65) Prior Publication Data

US 2020/0149394 A1 May 14, 2020

Related U.S. Application Data

(63) Continuation of application No. PCT/CN2018/099014, filed on Aug. 6, 2018.

(30) Foreign Application Priority Data

Aug. 8, 2017 (CN) .......................... 201710672003.3

(51) Int. Cl.
*E21B 49/06* (2006.01)
*E21B 49/00* (2006.01)
(Continued)

(52) U.S. Cl.
CPC .............. *E21B 49/005* (2013.01); *E21B 7/04* (2013.01); *E21B 7/046* (2013.01); *E21B 21/066* (2013.01); *G01V 5/085* (2013.01)

(58) Field of Classification Search
CPC .......... E21B 49/005; E21B 7/04; E21B 7/046; E21B 21/066; G01V 5/085; G01V 5/08; G01N 33/24
See application file for complete search history.

(56) References Cited

U.S. PATENT DOCUMENTS

2013/0192382 A1* 8/2013 Bois ..................... G01N 33/383
73/803
2014/0361466 A1* 12/2014 Kimour .................... G01N 1/36
264/496
(Continued)

FOREIGN PATENT DOCUMENTS

CN 201037829 Y 3/2008
CN 201522431 U 7/2010
(Continued)

OTHER PUBLICATIONS

Chen, Li et al, "Applications of scanning electron microscopy analytical techniques in earth sciences" Science China—Earth Science, vol. 45, No. 9, (2015), pp. 1347-1358, English Abstract is provided.

(Continued)

*Primary Examiner* — David P Porta
*Assistant Examiner* — Mamadou Faye
(74) *Attorney, Agent, or Firm* — J.C. Patents

(57) ABSTRACT

The present disclosure belongs to the field of petroleum exploration and development and, in particular, relates to a system and a method for analyzing while-drilling rock fragments in oil and gas field. The system includes a sample preparation mold and a sample scanning apparatus; the mold is configured to quickly batch prepare fragments into scan-
(Continued)

ning ready samples; the apparatus is portable and configured for batch scanning and analyzing the samples, and having the capabilities of anti-vibration, temperature control, dust prevention, and adaptability to a harsh well site environment; the method includes a scanning step where surface images, elements and mineral types of rock can be rapidly quantitatively analyzed, and lithologies thereof can be identified; the method also includes the analysis step in which rock's elastic parameters and target zone of the vertical well are determined, and geosteering and design of staged fracturing of horizontal well can be provided.

11 Claims, 10 Drawing Sheets

(51) Int. Cl.
 *E21B 7/04* (2006.01)
 *E21B 21/06* (2006.01)
 *G01V 5/08* (2006.01)

(56) References Cited

U.S. PATENT DOCUMENTS

2017/0152728 A1* 6/2017 Abou-Sayed ............ E21B 47/00
2018/0371892 A1* 12/2018 Shahan .................... F16F 15/02

FOREIGN PATENT DOCUMENTS

| | | |
|---|---|---|
| CN | 102169061 A | 8/2011 |
| CN | 102221550 A | 10/2011 |
| CN | 202256709 U | 5/2012 |
| CN | 203720098 U | 7/2014 |
| CN | 203732339 U | 7/2014 |
| CN | 104119048 A | 10/2014 |
| CN | 105067406 A | 11/2015 |
| CN | 105067649 A | 11/2015 |
| CN | 204903371 U | 12/2015 |
| CN | 106150490 A | 11/2016 |
| CN | 106261145 A | 1/2017 |
| CN | 106841260 A | 6/2017 |
| CN | 107620593 A | 1/2018 |
| WO | 2015/006670 A1 | 1/2015 |

OTHER PUBLICATIONS

The International Search Report of corresponding International application No. PCT/CN2018/099014, dated Oct. 26, 2018.

The Chinese First Examination Report and Search Report of corresponding Chinese application No. 201710672003.3, dated Apr. 27, 2018.

The Chinese Second Examination Report and Search Report of corresponding Chinese application No. 201710672003.3, dated Jun. 20, 2018.

* cited by examiner

101

SYSTEM AND METHOD FOR SCANNING WHILE-DRILLING ROCK FRAGMENTS IN AN OIL AND GAS FIELD

CROSS-REFERENCE TO RELATED APPLICATIONS

This application is a continuation of International Application No. PCT/CN2018/099014, filed on Aug. 6, 2018, which claims priority to Chinese Patent Application 201710672003.3, filed on Aug. 8, 2017, both of which are hereby incorporated by reference in their entireties.

TECHNICAL FIELD

The present disclosure belongs to the field of petroleum and natural gas exploration and development and, in particular, relates to a system and a method for scanning while-drilling rock fragments in an oil and gas field.

BACKGROUND

In recent years, with the advances of oil and gas exploration, unconventional oil and gas, such as shale oil and gas and tight oil and gas and so on, has been paid more and more attention, and becomes key to changing global petroleum energy pattern. The unconventional oil and gas is developing rapidly, and commercial exploration of the tight oil and gas, and the shale oil and gas is becoming more mature, and the proportion of the unconventional oil and gas in petroleum resources is also increasing. Therefore, it is very important to accelerate exploration and development of the unconventional oil and gas. As reservoir stratums of the unconventional oil and gas are usually very dense, explorers need to go deep from conventional scale to micro-nano scale. Thus accurately and quickly figuring out structures of pores and fractures at micro-nano scale, mineral content, lithologies and elastic mechanical properties of unconventional reservoirs are important for early resource evaluation, medium-term drilling guidance and final-period fracturing transformation production.

At present, the micro-nano scale researches on unconventional reservoirs are mainly concentrated in in-house laboratories, the samples that measured are rock cores of drilling. SEM, FIB-SEM, micro-CT, adsorption, etc are being used as testing methods. Although these testing methods have advantages of high testing resolution and rapid testing speed in the samples collection and testing process, the following problems are also exist: 1) the cost of collecting rock cores is high, and batch testing is expensive; 2) sample preparation is complicated, instruments are heavy and unportable, and cannot be used under a wild testing environment.

At present, in a drilling site, minerals, elements, lithologies and pore structure of reservoirs are mainly analyzed by portable testing instruments such as mud logging instruments, line logging instruments, XRD and XRF, these portable testing instruments have advantages such as simple sample preparation, easy to carry, strong wild adaptability, rapid testing speed and real-time guiding sitework.

However, there are still issues when using these testing instruments in the prior art for the analysis of minerals, elements, lithologies and structures of pores in the drilling site:

1) the accuracy of wild testing is poor and real information of stratums cannot be accurately reflected, as the low testing accuracy of existing portable testing instruments and the limitation of testing principle of these instruments;

2) with the upgrade of drilling technology (such as drill bit), PDC drill bit or air drill bit are used in drilling, however, the drilling rock fragments they created are too small to be seen by naked eye, which seriously affected the accuracy of lithologies of stratums decided by the field technicians;

3) existing drilling field analysis instruments cannot achieve full-automatic identification and quantitative analysis of minerals, and cannot achieve full-automatic identification of lithologies;

4) as for years rock fragment logging is performed by human subjective judgment, which has many limitations, thus full-automatic qualitative and quantitative identification of lithologies are needed;

5) there is no method for calculating elastic mechanical parameters using rock fragments samples in the prior art;

6) there is no technical method for real-time guiding drilling and oil and gas field exploration and development using rock fragments samples.

Therefore, there is a need for a scanning system and a technical method, which have the advantages for simple sample preparation procedures, easy to carry, suitable for a harsh well-site environment, high testing accuracy; and have the ability of quick quantitatively analysis of the surface structure, elements and minerals of rock, quick identification of the lithologies, calculation of the elastic mechanical parameters, as well as real-time guiding of the on-site drilling and oil and gas field exploration and development.

SUMMARY

In view of the above problems, the present disclosure provides a system for scanning while-drilling rock fragments in an oil and gas field. The scanning system includes a sample preparation mold and a rock fragments scanning apparatus. And small rock fragments samples generated during a while-drilling process in an oil and gas field can be quickly batch prepared into large-area scanning samples by the sample preparation mold. A batch scanning analysis may be performed by using the rock fragments scanning apparatus. The system for scanning while-drilling rock fragments, which is portable, not only has the capabilities for anti-vibration, temperature control and dust prevention, but also has strong adaptability to a harsh well site environment.

Another object of the present disclosure is to provide a method for scanning and analyzing the while-drilling rock fragments in an oil and gas field, which may quickly and full-automatically perform quantitative analysis of the surface structure, elements and minerals of rock, and quick identification of lithologies, a centimeter-scale large field image and elastic mechanical parameters can be obtained. The method also comprises selecting a target layer of a vertical well for development, assisting geosteering of horizontal well drilling and design of a staged fracturing scheme of horizontal well exploring, thus real-time guiding of the on-site drilling and oil and gas field exploration and development can be achieved.

The present disclosure is achieved by the following technical solutions:

A system for scanning while-drilling rock fragments in an oil and gas field, including a sample preparation mold and a rock fragments scanning apparatus;

the sample preparation mold is configured to quickly batch preparing small rock fragments samples generated during a while-drilling process in an oil and gas field into large-area scanning samples, and an acquisition cost of the scanning samples is able to be greatly reduced by using the small rock fragments samples to prepare the scanning samples;

the rock fragments scanning apparatus is configured to perform batch scanning and analyzing of the scanning samples in an oil and gas field, and the rock fragments scanning apparatus includes:

a structural unit configured to fix hardware of the rock fragments scanning apparatus, and the structural unit includes a temperature control sub-unit and an anti-vibration sub-unit, which enable the rock fragments scanning apparatus to be normally operated under a harsh environment of high temperature and vibration;

a scanning unit configured to perform canning and analyzing of the scanning samples;

a control unit configured to control a scanning process of the scanning unit;

a housing unit configured to protect internal hardware of the rock fragments scanning apparatus so as to realize quick disassembly and dust prevention.

Further, the sample preparation mold, which is durable and easy for a resin to cool and dissipate heat and made of stainless steel, enables the small rock fragments samples to be quickly batch prepared into the scanning samples.

Further, the sample preparation mold includes a first mold body and a second mold body, side surfaces of the first mold body and the second mold body are provided with a buckle apparatus, and opening and closing the buckle apparatus enables the first mold body and the second mold body to be assembled and disassembled;

the first mold body and the second mold body each includes a plurality of half-holes, and when the first mold body and the second mold body are assembled, the half-holes of the first mold body and the half-holes of the second mold body are in one-to-one correspondence to form a plurality of sample preparation holes; a depth of the sample preparation holes is smaller than a height of the sample preparation mold;

bottom surfaces of the first mold body and the second mold body include positioning hole caps to realize assembling and positioning of the first mold body and the second mold body.

Further, a process of preparing small rock fragments samples generated during the while-drilling process in the oil and gas field into the large-area scanning samples by using the sample preparation mold is specifically as follows:

while-drilling rock fragments collecting: collecting the while-drilling rock fragments of a target layer that returned to a ground together with a drilling mud;

while-drilling rock fragments screening and classifying: first using a sieve with large sieve pores to remove the while-drilling rock fragments with large particle size of a non-target layer that may fall from a well wall, and then using a sieve with small sieve pores to remove the while-drilling rock fragments with too small particle size to analyze, the while-drilling rock fragments with a particle size of 40 to 200 meshes are screened as samples to be tested;

washing: washing and drying the samples to be tested; a washing method is determined according to a composition of the drilling mud, and the while-drilling rock fragments of an oil-based drilling mud is washed with an oil displacement agent for several times, then washed with water and dried, and the while-drilling rock fragments of a water-based drilling mud is directly washed with water, then dried, the washed samples thereby are obtained;

resin injection molding: putting the washed samples into the sample preparation holes of the sample preparation mold, then quickly pouring resin ab glues into the sample preparation holes, and quickly stirring the washed samples and the resin ab glues, after standing, the rock fragments of the washed samples and the resin ab glues are cured together, then the scanning samples are prepared. And the powdered small rock fragments samples may be reprocessed into centimeter-scale large-area scanning samples by the curing action of the resin ab glues, which enables the waste rock fragments being converted into useful material, thereby realizing an utilization value equivalent to rock core samples.

polishing: polishing the prepared scanning samples with a mechanical polishing machine until the scanning fragments have very flat and smooth surfaces, then polished samples are obtained;

coating conductive layers: coating conductive layers on surfaces of the polished samples.

Further, the structural unit includes:

a structural skeleton configured to fix and protect hardware devices in the rock fragments scanning apparatus, the structural skeleton is made of a stainless steel material, and comprises three horizontally arranged plate-like structures and a plurality of vertically arranged columnar structures connected to the plate-like structures, and the structural skeleton is a rectangular structure comprising an upper structure and a lower structure;

a locking caster disposed on a bottom of the structural skeleton for moving the rock fragments scanning apparatus;

a sliding rail drawer disposed in the lower structure of the structural skeleton;

the anti-vibration sub-unit disposed on a bottom of the sliding rail drawer for reducing the influence of drilling vibration in a drilling site on the quality of a scanned image;

the temperature control sub-unit disposed on the upper structure and the lower structure of the structural skeleton, is composed of a plurality of fans and used for dissipating heat generated by the rock fragments scanning apparatus outside so as to improve adaptability of the rock fragments scanning apparatus to a high temperature environment such as a wild desert, and ensure normal operation of the hardware devices.

Further, the scanning unit includes:

a scanning and detecting system chamber disposed in the upper structure of the structural skeleton for maintaining a vacuum environment, and a backscattering electron probe, a secondary electron probe, a EDS spectrum probe, and a sample table are disposed inside the scanning and detecting system chamber; wherein the backscattered electron probe is configured to collect a backscattered electron signal, the secondary electron probe is configured to collect a secondary electronic signal, the EDS spectrum probe is configured to collect an x-ray signal, and the sample table is a full-automatic motor sample table capable of loading a plurality of samples;

an electron gun and a lens barrel, wherein the electron gun is configured to provide a high-energy focused electron beam, and disposed on a top of the upper structure of the structural skeleton; one end of the lens barrel is accommodated in the scanning and detecting system chamber for focusing the electron beam and aligning the focused electron beam to the sample table;

a vacuum pump configured to achieve evacuation of the scanning and detecting system chamber.

Further, the control unit includes:

a scanning control subunit configured to control the electron gun, the lens barrel, the backscattered electron probe, the secondary electron probe, the EDS spectrum probe, and the sample table, and disposed on a side surface of the upper structure of the structural skeleton, wherein the scanning control subunit is of plate-like structure, a 90 degree connector is provided at a bottom of the plate-like structure of the scanning control subunit for pulling the scanning control subunit with a plate-like structure from a vertical state to a horizontal state so as to facilitate inspection and maintenance of the scanning control subunit;

a software control subunit configured to implement control of all software and hardware, data storage and transmission, and disposed in the sliding rail drawer;

an input subunit through which an operator is able to set scan parameters;

a display subunit configured to display a scanning result.

Further, the housing unit includes:

a housing panel and a frame, the housing panel is a main package sub-unit of the housing unit, and is of a double-layer structure, and is made of an aluminum alloy material, and the housing panel and the frame are used together to realize quick disassembly and assembly;

buckles and block grooves disposed on the housing panel and the frame, and the buckles and the block grooves are used together to make portions of the housing unit to be mutually connected and the housing unit is fixed on the structural skeleton;

a dust prevention subunit configured for preventing dust, and including a dust prevention filter, and disposed at a position corresponding to the temperature control sub-unit, and the dust prevention sub-unit is able to be used as a heat dissipation passage of the temperature control sub-unit;

a sample chamber cover for loading and unloading a sample, a power switch cover for protecting a switch button, an electron gun cover for replacing an electron gun filament, and a software control subunit cover for shielding the software control subunit; all covers are disposed on the housing panel, and have buckles capable of being rotatably opened and closed.

A method for scanning and analyzing while-drilling rock fragments in an oil and gas field, using the system for scanning the while-drilling rock fragments in the oil and gas field, and the method includes a scanning step and an analysis step;

the scanning step is configured to perform scanning by using the system for scanning the while-drilling rock fragments in the oil and gas field to complete batch scanning tests of scanning samples of rock fragments, and obtain scanning test results of the scanning samples;

the analysis step includes an elastic mechanical parameters calculation substep and an oil and gas field application substep;

in the elastic mechanical parameters calculation substep, the elastic mechanical parameters is calculated by using the scanning test results of the scanning samples;

in the oil and gas field application substep, a target layer of a vertical well for development is selected by the system; and geosteering of horizontal well drilling and design of a staged fracturing scheme of horizontal well exploring are assisted by the system.

Further, the scanning step completes a centimeter-scale large field scanning of a sample by separately scanning each subarea, and the scanning step includes in turn:

loading the scanning samples, setting a scanning area of one scanning sample, selecting a subarea for scanning, obtaining a backscattered electron image of the subarea by using the backscattering electron probe, obtaining a secondary electron image of the subarea by using the secondary electron probe, removing a non-rock fragments visual field in the subarea, obtaining X-ray information of the subarea by using the EDS spectrum probe, automatically identifying and quantitatively analyzing elements in the subarea, automatically identifying and quantitatively analyzing minerals in the subarea by using a mineral database and obtaining a mineral image of the subarea, selecting a next subarea for scanning, after completing scanning of all subareas, automatically identifying lithologies of the scanning sample by using a lithologies database, turning to a next scanning sample for scanning, after completing scanning of all scanning samples, reloading a new batch of scanning samples for scanning.

Further, the elastic mechanical parameters calculation substep is specifically:

mosaicking backscattered electron images, secondary electron images and mineral images of a series of subareas together by an image mosaic software to obtain a backscattered electron image, a secondary electron image and a mineral image of a centimeter-scale large field;

quantitatively analyzing a surface structure of the scanning sample by using the backscattered electron image of the centimeter-scale large field or the secondary electron image of the centimeter-scale large field to obtain surface structure quantitative analysis data;

quantitatively analyzing minerals contents of the scanning sample by using the mineral image of the centimeter-scale large visual field to obtain mineral quantitative analysis data;

calculating the elastic mechanical parameters according to an equivalent medium model in combination with the surface structure quantitative analysis data and the mineral quantitative analysis data.

And the equivalent medium model refers to using elastic mechanical parameters of minerals and a structure itself combined with a proportion relationship of the minerals and the structure to determine the elastic mechanical parameters of the scanning samples of rock, such as Young's module and Poison ratio etc.

Further, the target layer of a vertical well for development is selected by the system comprising:

sampling the rock fragments of a vertical well of a certain block at equal intervals of a depth of the vertical well, completing preparation and scanning of the scanning samples of rock fragments to obtain data of lithologies, minerals, elements and elastic mechanical parameters corresponding to the depth of the vertical well;

drawing the obtained data of lithologies, minerals, elements and elastic mechanical parameters into vertical well pillars corresponding to the depth of the vertical well;

dividing the vertical well pillars into different sections according to different trend of the data of lithologies, minerals, elements and elastic mechanical parameters corresponding to the depth of the vertical well;

analyzing the different sections of the vertical well pillars to determine the target layer for development.

Further, the geosteering of horizontal well drilling and design of a staged fracturing scheme of horizontal well exploring are assisted by the system comprising:

utilizing a drilling system to perform horizontal well drilling on the selected target layer of a vertical well for development, and collecting rock fragments during the horizontal well drilling at equal intervals of a depth of a horizontal well;

completing preparation and scanning of scanning samples of rock fragments of horizontal well, and obtaining data of lithologies, minerals, elements and elastic mechanical parameters corresponding to the depth of the horizontal well;

drawing the data of lithologies, minerals, elements and elastic mechanical parameters obtained from the vertical well into vertical well pillars, and marking the target layer of a vertical well for development;

drawing data of lithologies, minerals, elements and elastic mechanical parameters obtained by the horizontal well drilling into horizontal well pillars in real time, comparing the horizontal well pillars with the vertical well pillars, detecting an accurate section of the horizontal well drilling in real time, timely adjusting a direction of horizontal well drilling to ensure accurate drilling of the drill bit at the target layer, thus the geosteering of horizontal well drilling is assisted;

after completion of the horizontal well drilling, the horizontal well pillars are able to be used as an important basis for the design of a staged fracturing scheme of horizontal well drilling; the horizontal well pillars are able to be used for staged fracturing scheme development of horizontal well exploring of shale gas so as to improve accuracy and profits of oil and gas exploration, and the horizontal well pillars are able to be used for calibrating mud logging well pillars and line logging well pillars so as to improve accuracy of mud logging and line logging.

Advantageous technical effects of the present disclosure:

(1) In the method provided by the present disclosure, the sample preparation mold can be used to quickly batch prepare small rock fragments samples generated during an while-drilling process in an oil and gas field into large-area scanning samples such that the sample preparation process is simple and rapid. And the rock fragments generated while drilling in a drilling process are fully utilized as scanning samples, thus the waste rock fragments samples are turned into useful materials, which not only overcomes the limitation that rock fragments can only be judged by naked eye during mud logging of traditional methods, but also avoids the process of rock core collecting, and needs no additional steps for collecting test samples, greatly reducing an acquisition cost of the scanning samples;

(2) The rock fragments scanning apparatus provided in the method of the present disclosure can perform batch scanning and analyzing of the scanning samples. The system for scanning while-drilling rock fragments, which is portable, not only can be configured for anti-vibration, temperature control and dust prevention, but also can be normally operated in a harsh well site environment (such as high temperature, dust, vibration), the wild well site operation of the system can be realized;

(3) the scanning step in the method provided by the present disclosure is very simple and high automatic, and quickly and full-automatically quantitative analysis of the surface structures, elements and minerals of rock as well as quick identification of the lithologies can be achieved, and the limitation that the existing technology cannot be used for automatic mineral quantitative analysis and automatic lithology identification in a wild drilling site can be overcome;

(4) the method provided by the present disclosure uses rock fragments samples to calculate elastic mechanical parameters, and the calculated elastic mechanical parameters are important for developing and fracturing of an oil and gas well;

(5) the scanning data obtained by the present disclosure can be applied to an oil and gas field, such as selecting a target layer of a vertical well for development, assisting the geosteering of horizontal well drilling and the design of a staged fracturing scheme of horizontal well exploring, thereby improving accuracy and efficiency of oil and gas exploration.

(6) In the prior art, there is no technical method using rock fragments samples to real-time guide drilling and oil and gas field exploration and development. In the present disclosure, the cost of sample preparation can be reduced by using the while-drilling rock fragments, and the cost of testing can be greatly reduced by performing batch automatic testing by the rock fragments scanning apparatus of the present disclosure. The accuracy of oil and gas exploration also can be greatly improved by the system and method of present disclosure.

Figure 1A:
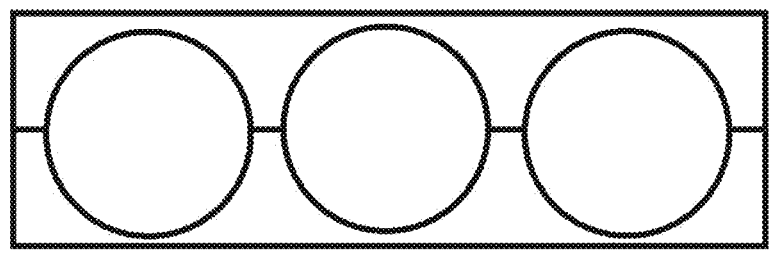
FIG. 1a is a top view of a sample preparation mold according to an embodiment of the present disclosure.
Figure 1B:
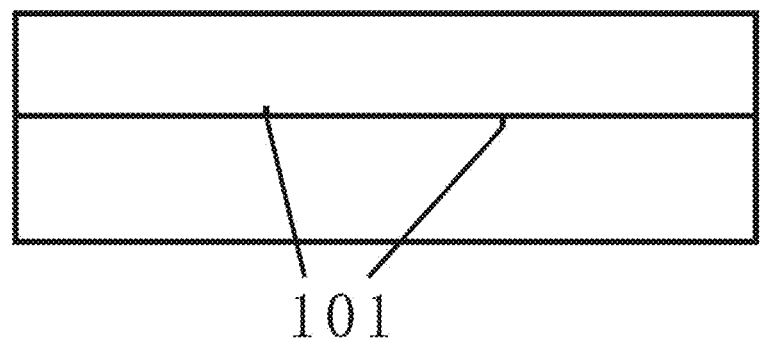
FIG. 1b is a bottom view of a sample preparation mold according to an embodiment of the present disclosure.
Figure 1C:
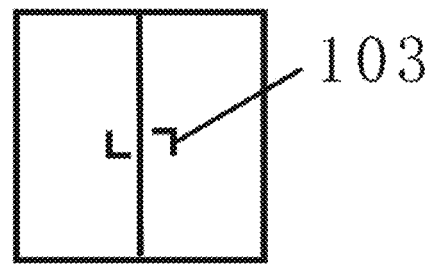
FIG. 1c is a side view of a sample preparation mold according to an embodiment of the present disclosure.
Figure 1D:
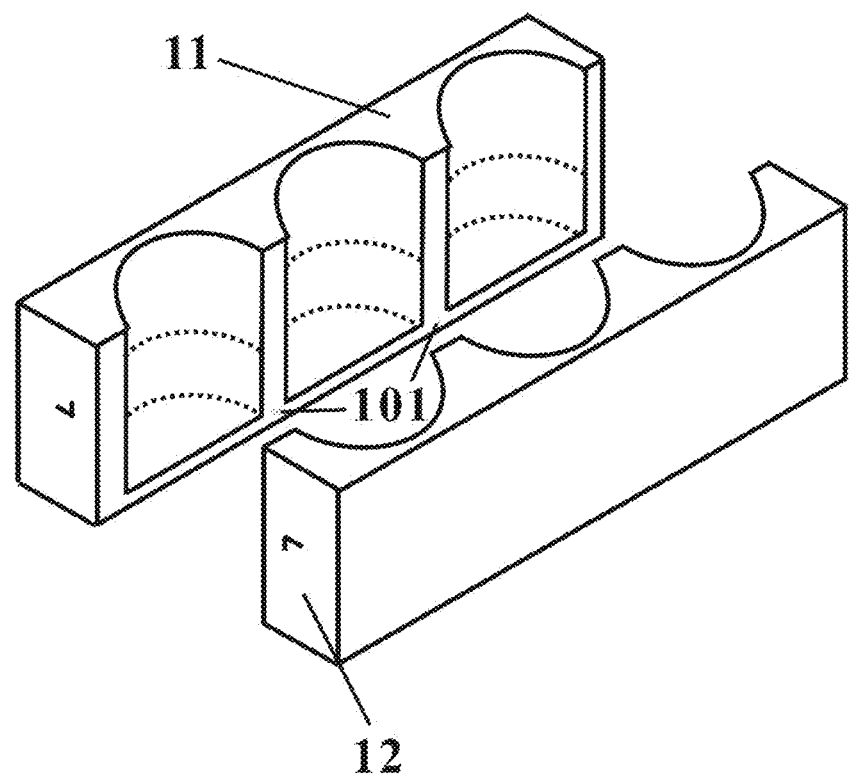
FIG. 1d is a three-dimensional schematic diagram of a sample preparation mold according to an embodiment of the present disclosure.

List of reference numbers: 101: positioning hole cap, 103: buckle apparatus, 11: first mold body, 12: second mold body, 104: resin AB glue, 105: rock fragments, 401: structural skeleton, 402: locking caster, 403: anti-vibration sub-unit, 404: sliding rail drawer, 405: electron gun, 406: lens barrel, 407: electron gun filament replacement port, 408: scanning and detecting system chamber, 409: secondary electron probe, 410: backscattered electrons probe, 411: EDS spectrum probe, 412: sample table, 413: scanning control sub-unit, 414: temperature control sub-unit, 415: software control subunit, 416: display subunit, 417: input subunit, 418: power and data interface, 419: vacuum pump, 501: housing panel, 502: housing frame, 503: handle, 504: sample chamber cover, 505: power switch cover, 506: electron gun cover, 507: block groove, 508: buckle, 509: dust prevention sub-unit, 510: software control subunit cover, 601: scanning range, 602: matrix scanning area, 603: the $12^{th}$ scanning subarea, 604: backscattered electron image of the 12$^{th}$ subarea, 605: secondary electron image of the 12$^{th}$ subarea, 606: scanning visual field of the 12$^{th}$ subarea with non-rock fragment been removed, 607: mineral database, 608: mineral distribution image of the 12$^{th}$ subarea, 609: lithologies database, 801: drilling rig, 802: drilling pipe, 803: drilling bit, 804: system for scanning while-drilling rock fragments in an oil and gas field, 805: vertical well pillars, 806: horizontal well pillars.

DESCRIPTION OF EMBODIMENTS

To make the objectives, technical solutions, and advantages of the present disclosure clearer, the following clearly describes the present disclosure in detail with reference to the accompanying drawings and embodiments. It is understood that the specific embodiments described herein are merely illustrative of the present disclosure and are not intended to limit the present disclosure.

On the contrary, the present disclosure covers any alternatives, modifications, equivalents and embodiments done within the spirit and range of the present disclosure defined by the claim. Further, in order to make the present disclosure better known to the public, some specific details are described in detail in the detailed description of the present disclosure. For persons of ordinary skill in the art, the present disclosure may be fully understood without a description of these details.

The existing problems in the prior art are that on the one hand, the cost of collecting rock cores is high; on the other hand, in the existing test methods, sample preparation is complicated, instruments are heavy and difficult to move, and the instruments cannot be adapted to a wild testing environment.

In view of the above technical problems, an embodiment of the present disclosure provides a system for scanning while-drilling rock fragments in an oil and gas field, including a sample preparation mold and a rock fragments scanning apparatus, the sample preparation mold is configured to quickly batch preparing small rock fragments samples generated during a while-drilling process in an oil and gas field into large-area scanning samples, and the waste rock fragments samples are turned into useful materials, which greatly reduces an acquisition cost of the scanning samples. The rock fragments scanning apparatus is configured to perform batch scanning and analyzing of the scanning samples in an oil and gas field, and the rock fragments scanning apparatus includes four parts: a structural unit configured to fix hardware of the rock fragments scanning apparatus, and the structural unit includes a temperature control sub-unit and an anti-vibration sub-unit, which enable the rock fragments scanning apparatus to be normally operated under a harsh environment of high temperature and vibration; a scanning unit configured to perform canning and analyzing of the scanning samples; a control unit configured to control a scanning process of the scanning unit; a housing unit configured to protect internal hardware of the rock fragments scanning apparatus so as to realize quick disassembly and dust prevention.

Using the sample preparation mold can make a sample preparation process simple and rapid, and can make the while-drilling rock fragments generated in a drilling process to be fully utilized as a scanning sample, avoiding the process of rock core collection and high cost of rock core collection, zero cost of sample collection can be realized.

In a specific embodiment, the sample preparation mold is made of stainless steel or other materials, and the selected material needs to be durable and easy for resin ab glue to cool and dissipate heat. In this embodiment, the sample preparation mold includes three cylindrical sample preparation holes, and three samples may be prepared at the same time. Specifically, opening holes from a top section of the mold to obtain the sample preparation holes. And the depth of the sample preparation holes is smaller than the height of the sample preparation mold. The cylindrical sample preparation holes of the sample preparation mold have a diameter of 10-30 mm and a height of 5-10 mm. In other specific embodiments, the number of the cylindrical sample preparation holes is not limited to three, it may be any natural number, and the shape of the sample preparation holes is not limited to a cylindrical shape, it may be any shape such as a square or the like.

In this embodiment, the sample preparation mold is composed of two parts assembled from left to right or from right to left so as to facilitate demolding of a molded sample. As shown in FIGS. 1a-1d, the sample preparation mold includes a first mold body 11 and a second mold body 12, which are assembled from left to right, and side surfaces of the first mold body 11 and the second mold body 12 are provided with a buckle apparatus 103, and opening and closing of the buckle apparatus enables the first mold body and the second mold body to be assembled and disassembled; the first mold body and the second mold body each includes a plurality of half-holes, and when the first mold body and the second mold body are assembled, the half-holes of the first mold body and the half-holes of the second mold body are in one-to-one correspondence to form a plurality of sample preparation holes; bottom surfaces of the first mold body and the second mold body include positioning hole caps 101 to realize assembling and positioning of the first mold body and the second mold body.

Figure 2:
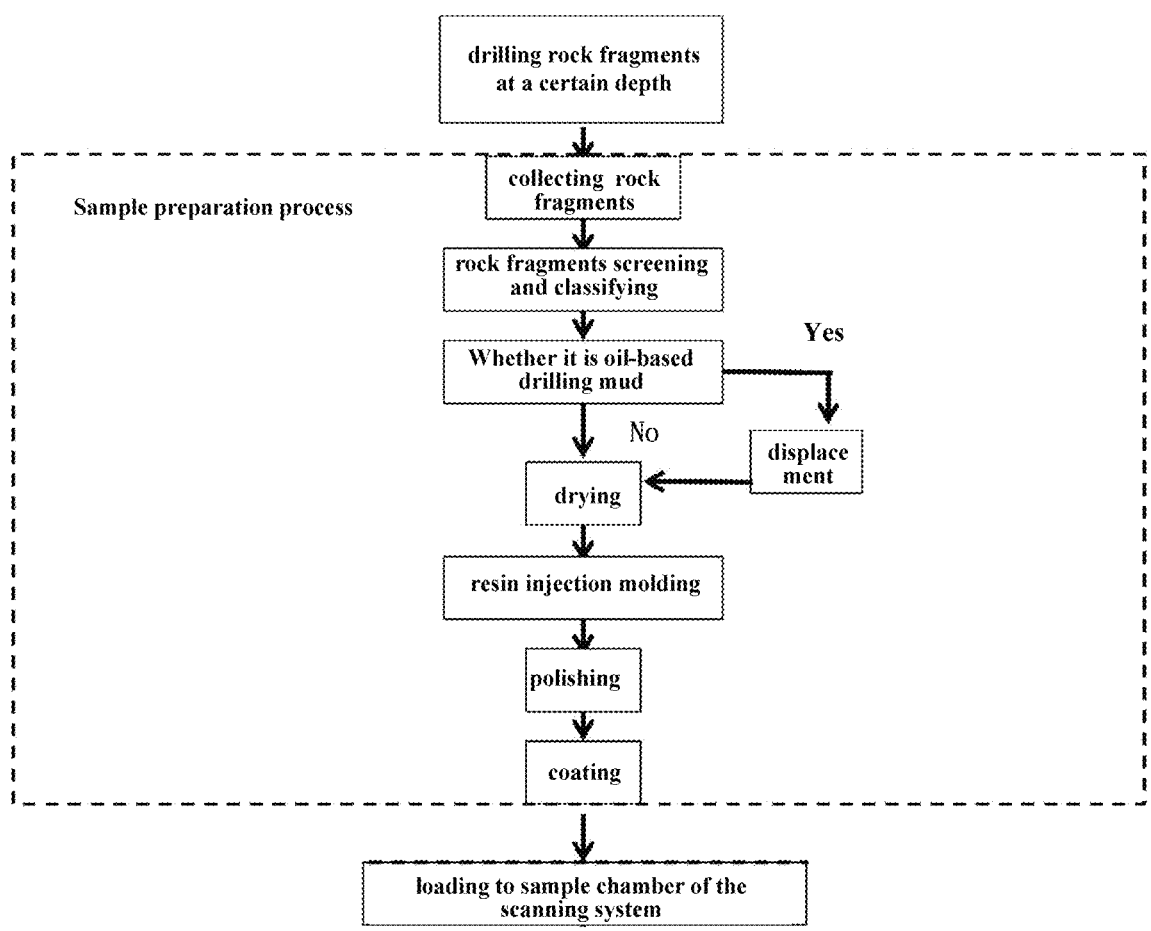
FIG. 2 is a flowchart of sample preparation according to an embodiment of the present disclosure
Figure 3:
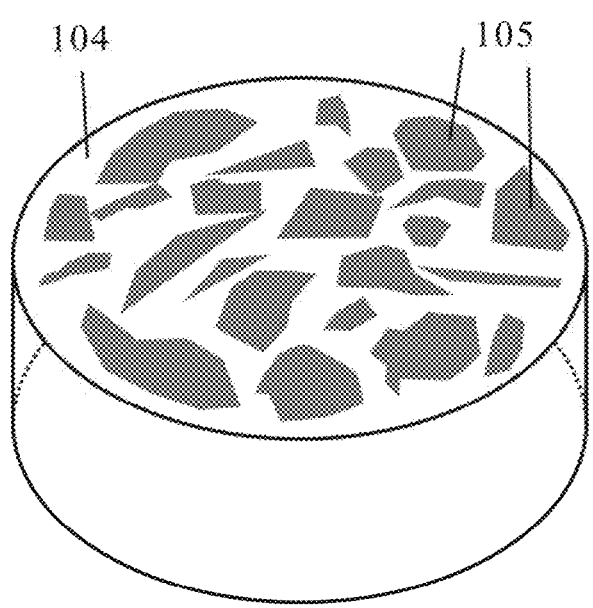
FIG. 3 is a schematic diagram of a molded sample according to an embodiment of the present disclosure.

As shown in FIG. 2, a sample preparation process using the sample preparation mold includes: collecting while-drilling rock fragments of a certain depth, screening and classifying the while-drilling rock fragments, washing and drying the while-drilling rock fragments, injecting resin for molding, polishing and coating. Specifically, the sample preparation process comprises:

while-drilling rock fragments collecting: collecting the while-drilling rock fragments of a target layer that returned to a ground together with a drilling mud; numbering the collected while-drilling rock fragments, in the embodiment of the present disclosure, the while-drilling rock fragments specifically refer to rock fragments, collected by a mud logging personnel at a drilling site of an oil and gas field, that return to a ground together with a drilling mud.

while-drilling rock fragments screening and classifying: comprising screening and classifying samples by selecting two sieves with different sizes of sieve pore, such as 40 mesh sieve and 200 mesh sieve, first using a sieve with large sieve pores to remove the while-drilling rock fragments with large particle size of a non-target layer that may fall from a well wall, and then using a sieve with small sieve pores to remove the while-drilling rock fragments with too small particle size to analyze, and finally retaining the while-drilling rock fragments with a certain particle size of the target layer, preferably, the while-drilling rock fragments with a particle size of 40 to 200 meshes are screened as samples to be tested;

washing: washing and drying the samples to be tested; a washing method is determined according to a composition of the drilling mud, and the while-drilling rock fragments of an oil-based drilling mud is washed with an oil displacement agent for several times, then washed with water and dried, and the while-drilling rock fragments of a water-based drilling mud is directly washed with water, then dried, the washed samples thereby are obtained;

resin injection molding: putting the washed samples into the sample preparation holes of the sample preparation mold, then quickly pouring resin ab glues into the sample preparation holes, and quickly stirring the washed samples and the resin ab glues, after standing, the rock fragments of the washed samples and the resin ab glues are cured together, then the scanning samples are prepared;

polishing: polishing the prepared scanning samples with a polishing machine until the scanning fragments have very flat surfaces, then polished samples are obtained;

coating conductive layers: coating carbon or gold onto surfaces of the polished samples, which is aimed to increase conductivity of the samples, improve scanning imaging quality and mineral analysis accuracy; as shown in FIG. 3, it is a schematic diagram of a polished sample obtained by sample preparation.

Where, the resin injection molding is performed by the following steps:

1) locking the buckle apparatus 103 to closely assemble left and right portions of the sample preparation mold, and accurately positioning the left and right portions of the sample preparation mold by using the positioning hole caps 101;

2) loading a small amount of the washed samples after drying into cylindrical sample preparation holes in the sample preparation mold, and quickly pouring an appropriate amount of mixed resin ab glue into the sample preparation holes;

3) quickly stirring the washed samples and the resin ab glue with a glass rod, and trying to make the largest sections of the washed samples facing down;

4) standing the sample preparation mold, and when the mold is restored to a normal temperature, the washed samples and the resin ab glue are cured together;

5) opening the buckle apparatus 103, and taking out the cured and molded sample, then the scanning samples are prepared, and a diameter of the scanning sample is 10-30 mm, a height is 5-10 mm.

Figure 4:
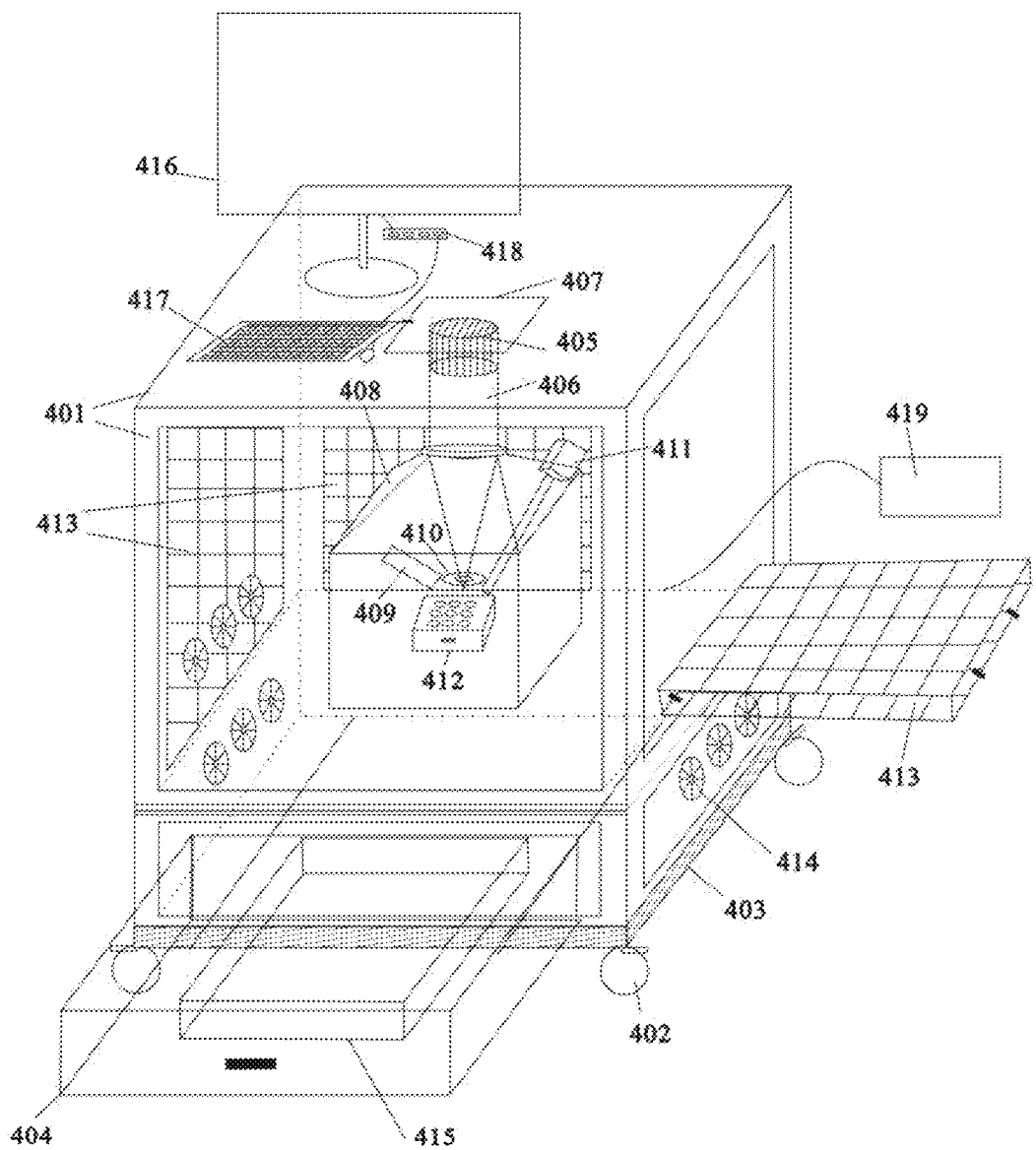
FIG. 4 is a three-dimensional schematic diagram of a structural unit, a scanning unit, and a control unit in a rock fragments scanning apparatus according to an embodiment of the present disclosure.
Figure 5A:
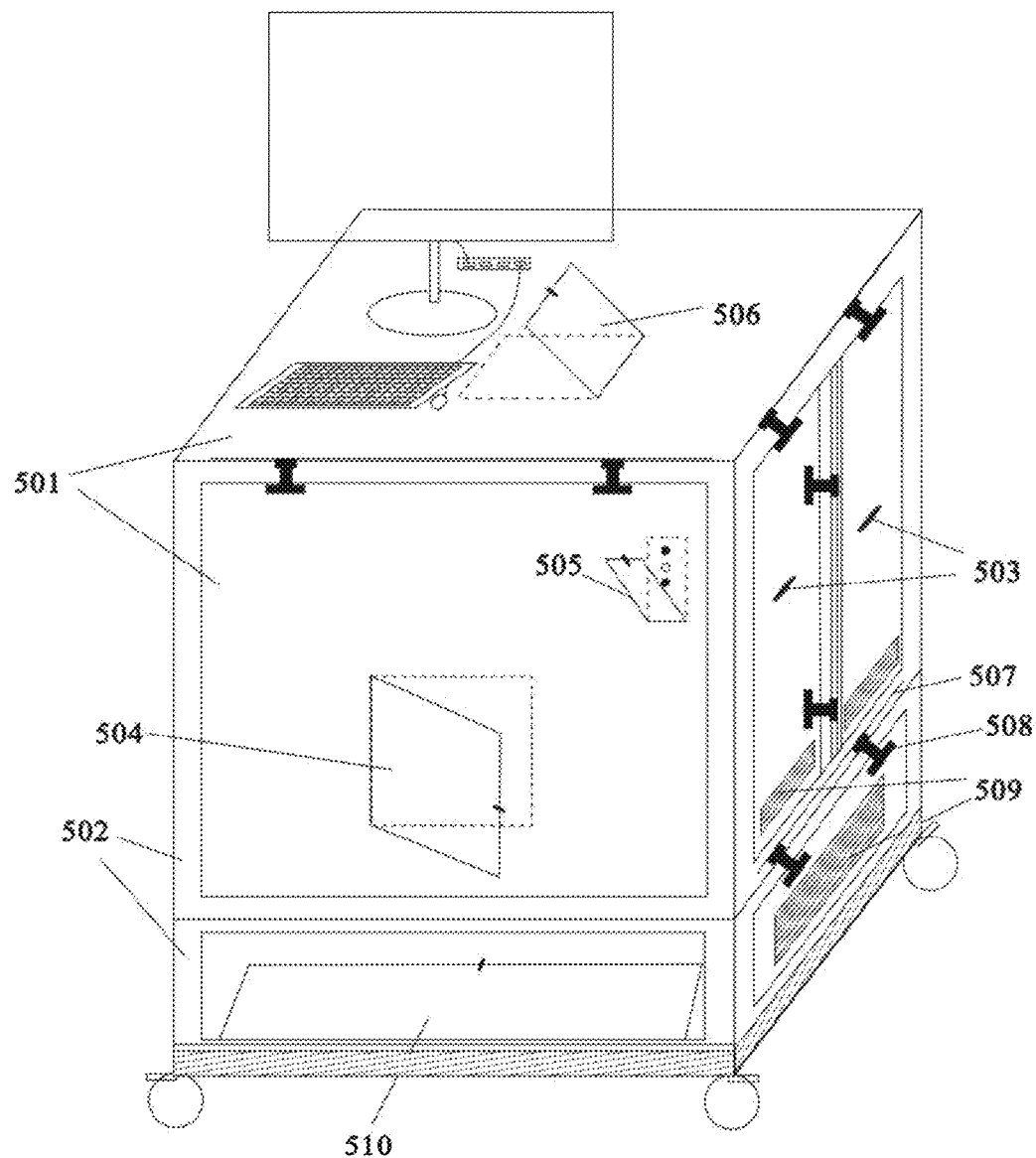
FIG. 5a is a three-dimensional schematic diagram of a rock fragments scanning apparatus (including a housing unit) according to an embodiment of the present disclosure.
Figure 5B:
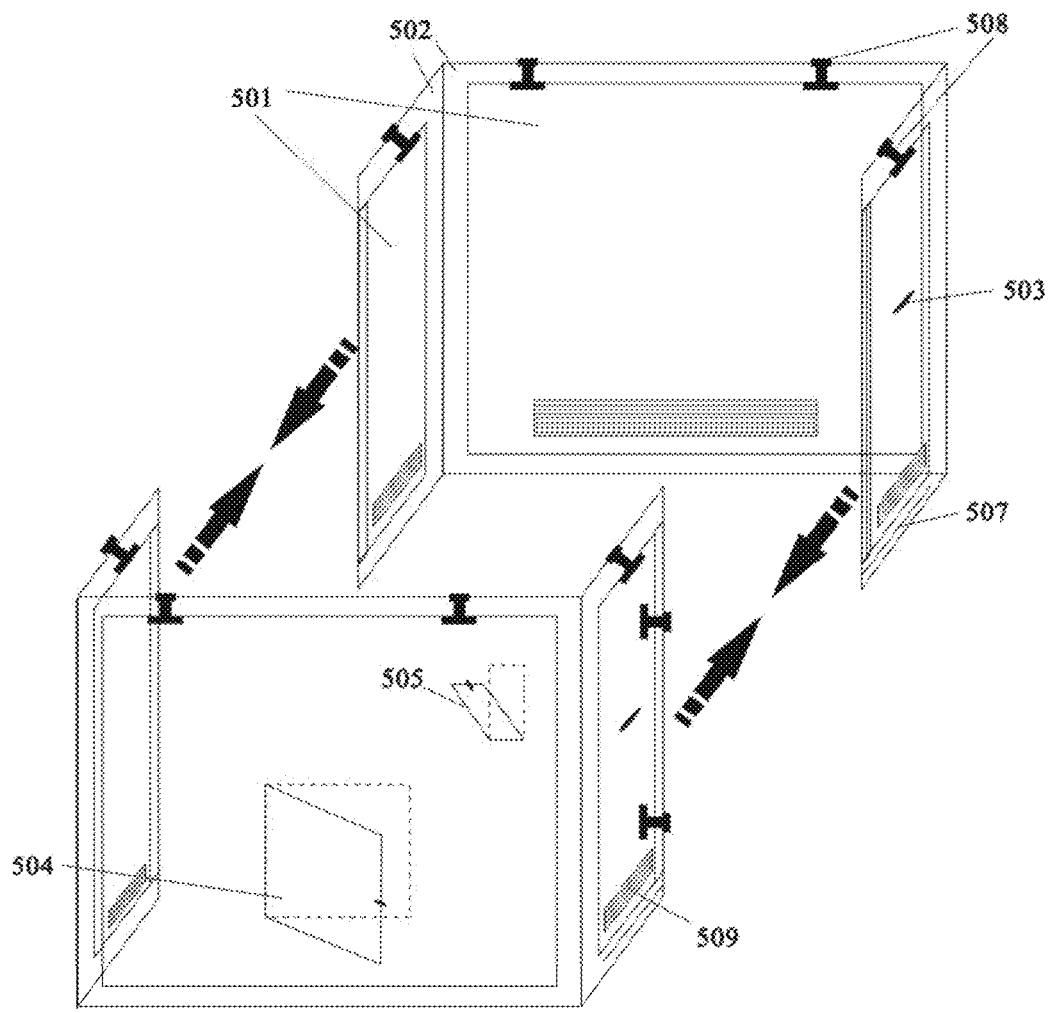
FIG. 5b is a three-dimensional schematic diagram of a middle portion of a housing unit being separated into two portions according to an embodiment of the present disclosure.

FIG. 4 is a three-dimensional schematic diagram of a structural unit, a scanning unit, and a control unit in a rock fragments scanning apparatus according to an embodiment of the present disclosure; FIG. 5a is a three-dimensional schematic diagram of a rock fragments scanning apparatus (including a housing unit) according to an embodiment of the present disclosure; FIG. 5b is a three-dimensional schematic diagram of a middle portion of a housing unit being separated into two portions according to an embodiment of the present disclosure. The rock fragments scanning apparatus provided by the embodiments of the present disclosure includes a structural unit, a scanning unit, a control unit and a housing unit.

The structural unit includes:

1) the structural skeleton 401 configured to fix and protect hardware devices in the system for scanning the while-drilling rock fragments in the oil and gas field, and is made of a stainless steel material and divided into an upper structure and a lower structure, and has a rectangular skeleton structure composed of three plate-like structures and a plurality of columnar structures.

2) a locking caster 402 configured to move the system for scanning the while-drilling rock fragments in the oil and gas field, and disposed on a bottom of the structural skeleton; the number of the locking caster may be four, and the locking caster has a large bearing capacity, and is silent, the casters are convenient to be locked and rolled, can be used for moving apparatus flexibly;

3) a sliding rail drawer 404 for loading a software control unit, and disposed in the lower structure of the structural skeleton;

4) an anti-vibration sub-unit 403 configured to reduce the influence of drilling vibration in a drilling site on the quality of a scanned image, and disposed on a bottom of the sliding rail drawer 404;

5) a temperature control sub-unit 414 configured to dissipate heat generated by the device outside, and is composed of a plurality of fans, and the fans are disposed in many places of the upper structure and the lower structure of the structural skeleton, thereby improving adaptability of the rock fragments scanning apparatus to a high temperature environment of a wild desert, and ensuring normal operation of the hardware devices.

The scanning unit includes:

1) a scanning and detecting system chamber 408 disposed in the upper structure of the structural skeleton for maintaining a vacuum environment, and a backscattering electron probe 410, a secondary electron probe 409, a EDS spectrum probe 411, and a sample table 412 are disposed inside the scanning and detecting system chamber; where the backscattered electron probe is configured to collect a backscattered electron signal, the secondary electron probe is configured to collect a secondary electronic signal, the EDS spectrum probe is configured to collect an x-ray signal, and the sample table is a full-automatic motor sample table capable of loading a plurality of samples, and the sample table is convenient to be used for moving, unloading and loading of the samples;

2) an electron gun 405 and a lens barrel 406, where the electron gun is configured to provide a high-energy focused electron beam, and is disposed on a top of the upper structure of the structural skeleton. a tungsten filament electron gun, $CeB_6$ or $LaB_6$ or the like may be selected as the electron gun; one end of the lens barrel is accommodated in the scanning and detecting system chamber for focusing the electron beam and aligning the focused electron beam to the sample table; where an electron gun filament replacement port 407 is disposed on the uppermost plate-like structure of the structural skeleton 401;

3) a vacuum pump 419 configured to complete evacuation of the scanning and detecting system chamber, and a turbo molecular pump or the like may be optionally used as the vacuum pump. Further, the vacuum pump is disposed outside the housing of the scanning apparatus.

The control unit includes:

1) a scanning control subunit 413 configured to control the electron gun, the lens barrel, the backscattered electron probe, the secondary electron probe, the EDS spectrum probe, and the sample table, and disposed on three side surfaces of the upper structure of the structural skeleton, where the scanning control subunit is of plate-like structure, a 90 degree connector is provided at a bottom of the plate-like structure of the scanning control subunit for pulling the scanning control subunit with a plate-like structure from a vertical state to a horizontal state so as to facilitate inspection and maintenance of the scanning control subunit;

2) a software control subunit 415 configured to implement control of all software and hardware, data storage and transmission, and disposed in the sliding rail drawer. In a specific embodiment, a computer host may be selected as the software control subunit; a bottom of the sliding rail drawer is provided with slidable rails, the computer host in the drawer can easily be removed out so as to facilitate inspection and maintenance of the host computer;

3) an input subunit 417 through which an operator is able to set scan parameters; in a specific embodiment, the input subunit 417 includes a mouse and a keyboard;

4) a display subunit 416 configured to display a scanning result, a power and data interface 418 are disposed on the display subunit, and the power and data interface 418 are provided with power and data transmission interfaces required for displaying the subunit.

Where, the display subunit and the input subunit may be put on the top of the structural skeleton.

The housing unit includes:

1) a housing panel 501 and a frame 502, the housing panel is a main package sub-unit of the housing unit, and is of a double-layer structure, and is made of an aluminum alloy material, and is very hard but low in weight, and can effectively block strong collision during a transportation process of the instrument so as to protect the rock fragments scanning apparatus. The housing panel 501 serves as a main panel of the entire instrument housing, and the housing frame 502 is configured to be connected with the housing panel, and the housing panel and the frame are used together to realize quick disassembly and assembly;

2) buckles 508 and block grooves 507 disposed on the housing panel and the frame, and the buckles and the block grooves are used together to make portions of the housing unit to be mutually connected and the housing unit is fixed on the structural skeleton; as shown in FIG. 5b, by opening the buckles 508 and the block grooves 507, the middle portion of the housing unit can be disassembled into two parts, and the detachable housing unit greatly facilitates inspection and maintenance of the hardware of the rock fragments scanning apparatus;

3) a dust prevention sub-unit 509 configured for preventing dust, and including a dust prevention filter, and disposed at a position corresponding to the temperature control sub-unit, and the dust prevention sub-unit is able to be used as a heat dissipation passage of the temperature control sub-unit; and the arrangement of the dust prevention sub-unit 509 effectively prevents external dust from going inside of the instrument and enhances adaptability of the instrument in a harsh environment such as a wild desert;

4) a sample chamber cover 504 for loading and unloading a sample, a power switch cover 505 for protecting a switch button, an electron gun cover 506 for replacing an electron gun filament, and a software control subunit cover 510 for shielding the software control subunit; all the covers are disposed on the housing panel, and are provided with buckles capable of being rotatably opened and closed, and the arrangement of the covers greatly facilitates inspection and maintenance of the scanner hardware.

In this embodiment, the housing unit is further provided with handles 503 so as to facilitate the handling of the instrument.

The system for scanning while-drilling rock fragments in an oil and gas field provided by the embodiment of the present disclosure has the following beneficial technical effects:

1) In the method provided by the present disclosure, the sample preparation mold can be used to quickly batch prepare small rock fragments samples generated during an while-drilling process in an oil and gas field into large-area scanning samples such that the sample preparation process is simple and rapid. And the rock fragments generated while drilling in a drilling process are fully utilized as scanning samples, thus the waste rock fragments samples are turned into useful materials, which not only overcomes the limitation that rock fragments can only be judged by naked eye during mud logging of traditional methods, but also avoids the process of rock core collecting, and needs no additional steps for collecting test samples, greatly reducing an acquisition cost of the scanning samples;

2) The system provided in the method of the present disclosure, which is portable (i.e. easy to be carried), is convenient to be inspected and maintained as the structure thereof is reasonably arranged, thus, the system not only can be used for anti-vibration, temperature control and dust prevention, but also can be normally operated in a harsh well site environment (such as high temperature, dust, vibration), the wild well site operation of the system can be realized.

3) The parts of the rock fragments scanning apparatus are reasonable arranged and small in volume, the portability of the rock fragments scanning apparatus to wild operation can be improved. As the structural unit and the housing unit are easy to be disassembled, it is convenient to inspect and maintain the instruments. The rock fragments scanning apparatus has a whole weight of less than 200 KG, and a volume of less than 1 m$^3$, and a backscattered and secondary electron image resolution of better than 500 nm, and a X-ray spatial resolution of about 1 um, and a single sample scanning time of less than 30 min, which can satisfy on-site rapid and high resolution test requirements.

The embodiment further provides a method for scanning and analyzing the while-drilling rock fragments in an oil and gas field, including a scanning step and an analysis step;

the scanning step is configured to perform detailed scanning by using the system for scanning while-drilling rock fragments in an oil and gas field to complete batch scanning tests of the scanning samples of rock fragments, and obtain scanning test results of the scanning samples;

the analysis step includes an elastic mechanical parameters calculation substep and an oil and gas field application substep;

in the elastic mechanical parameters calculation substep, the elastic mechanical parameters is calculated by using the scanning test results of the scanning samples;

the oil and gas field application substep specifies two applications scenarios in an oil and gas field: 1) selecting a target layer of a vertical well for development, and 2) assisting the geosteering of horizontal well drilling and the design of a staged fracturing scheme of horizontal well exploring.

Figure 6:
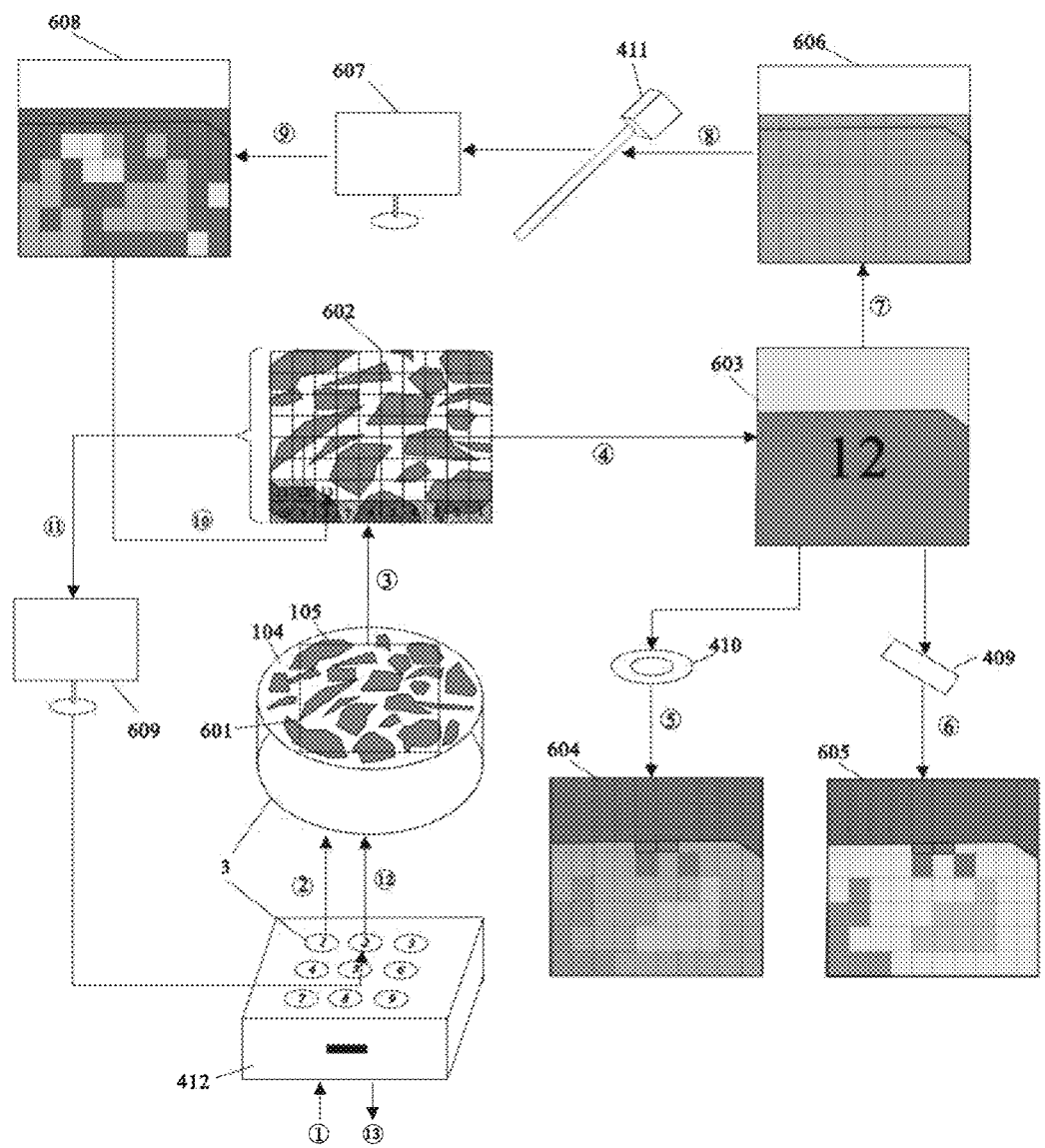
FIG. 6 is a flowchart of a scanning step in an embodiment of the present disclosure.

As shown in FIG. 6, the scanning step is specifically as follows:

loading nine scanning samples 3 on the sample block 412 at a time, opening the sample chamber cover 504 of the housing unit, loading the sample table into the scanning and detecting system chamber 408, closing the sample chamber cover, and vacuuming the scanning and detecting system chamber by the vacuum pump 419; where the number of scanning samples loaded on the sample table at one time can be adjusted as needed;

1) after reaching a required vacuum degree, turning on the electron gun and setting corresponding scanning parameters, and setting a scanning range 601 for all scanning samples;

2) selecting one scanning sample, matrixing the scanning range, and obtaining a scanning area 602;

3) selecting a full visual field of a certain scanning subarea (for example, the 12$^{th}$ scanning subarea 603 in FIG. 6) in a certain order;

4) obtaining a backscattered image of the scanning subarea by using the backscattering probe 410 (for example, a backscattered electron image 604 of the 12$^{th}$ scanning subarea in FIG. 6);

5) obtaining a secondary electron image of the scanning subarea by using the secondary electron probe 409 (for example, a secondary electron image 605 of the 12$^{th}$ scanning subarea in FIG. 6);

6) removing a non-rock fragment visual field in the scanning subarea (for example, a scanning visual field 606 with non-rock fragment removed of the 12$^{th}$ scanning subarea in FIG. 6);

7) obtaining X-ray information of the subarea by using the EDS spectrum probe 411, and automatically identifying and quantitatively analyzing elements in the subarea;

8) automatically identifying and quantitatively analyzing minerals in the subarea by using a mineral database 607 and obtaining a mineral image of the subarea (for example, a mineral distribution image 608 of the 12$^{th}$ scanning subarea in FIG. 6);

9) selecting a next subarea for scanning according to the above steps;

10) after completing scan of all subareas, automatically identifying lithologies of the sample by using a lithology database 609;

11) turning to a next scanning sample, and completing scan of all scanning samples in this batch according to the above steps;

12) after taking out this batch of scanning samples, reloading a new batch of scanning samples for scanning.

It should be noted that the scanning process of the present disclosure can be completed by one computer, and the operations are simple and highly automated, no intervention is needed once the parameters are set. The scanning process thus overcomes the defect that elements only can be semi-quantitative and semi-qualitative analyzed in traditional methods, full-automatic identification and quantitative analysis of elements can be achieved; the scanning process also overcomes the defect that minerals cannot be automatically identified and quantitatively analyzed at a drilling site in the traditional methods, and full-automatic identification and quantitative analysis of minerals can be realized; the scanning process further overcomes the defect that lithologies cannot be identified in the traditional methods, and full-automatic identification of lithologies can be achieved; the scanning process further overcomes the defect that a scanning range is small in the traditional methods, and a centimeter-scale large visual field scanning of a sample can be completed by scanning each of the subareas, separately.

The elastic mechanical parameter calculation substep is specifically:

mosaicking backscattered electron images, secondary electron images and mineral images of a series of subareas together by an image mosaic software to obtain a backscattered electron image, a secondary electron image and a mineral image of a centimeter-scale large visual field;

quantitatively analyzing a surface structure of the scanning sample by using the backscattered electron image of the centimeter-scale large visual field or the secondary electron image of the centimeter-scale large visual field to obtain surface structure quantitative analysis data;

quantitatively analyzing minerals contents of the scanning sample by using the mineral image of the centimeter-scale large visual field to obtain mineral quantitative analysis data;

calculating the elastic mechanical parameters according to an equivalent medium model in combination with the surface structure quantitative analysis data and the mineral quantitative analysis data, and the equivalent medium model refers to using elastic mechanical parameters of minerals and a structure itself in combined with a proportion relationship of the minerals and the structure to determine the elastic mechanical parameters of the scanning samples of rock fragments.

It should be noted that the surface structure analysis refers to the evaluation of porosity and pore size distribution of rock fragments, which may provide a basis for reservoir spatial characterization, oil and gas occurrence status research, and oil and gas resource assessment for an oil and gas reservoir stratum. Elements in the automatic identification and quantitative analysis include but not limited to K, S, V, Ni, Cu, U, and Th, which may reflect sedimentary environment and radioactivity of formation. Minerals in the automatic identification and quantitative analysis include but not limited to silicon minerals such as quartz and feldspar, carbonate minerals such as calcite and dolomite, clay minerals such as illite and chlorite, which may be used to analyze sedimentary environment, diagenetic evolution, and diagenetic facies. The lithologies include sedimentary rocks such as sandstone, carbonate rock and mudstone, metamorphic rocks such as quartzite and slate, magmatic rocks such as granite and basalt can be automatic identified. Accurate lithologies identification is important for stratigraphic division and oil and gas exploration of a complex reservoir stratum. Elastic mechanical parameters include elastic modulus, Poisson's ratio, brittleness index, wave velocity, etc. are calculated, which may provide a strong basis for drilling and completion optimization and fracturing treatment of the reservoir stratum.

Specifically, that the selecting a target layer of the vertical well for development is illustrated with reference to FIG. 7, the specific steps are:

sampling the rock fragments of a vertical well of a certain block at equal intervals of a depth of the vertical well, completing preparation and scanning of the scanning samples of rock fragments to obtain data of lithologies, minerals, elements and elastic mechanical parameters corresponding to the depth of the vertical well;

drawing the obtained data of lithologies, minerals, elements and elastic mechanical parameters into vertical well pillars corresponding to the depth of the vertical well;

dividing the vertical well pillars into different sections according to different trend of the data of lithologies, minerals, elements and elastic mechanical parameters corresponding to the depth of the vertical well;

analyzing the different sections of the vertical well pillars to determine the target layer for development.

Figure 7:
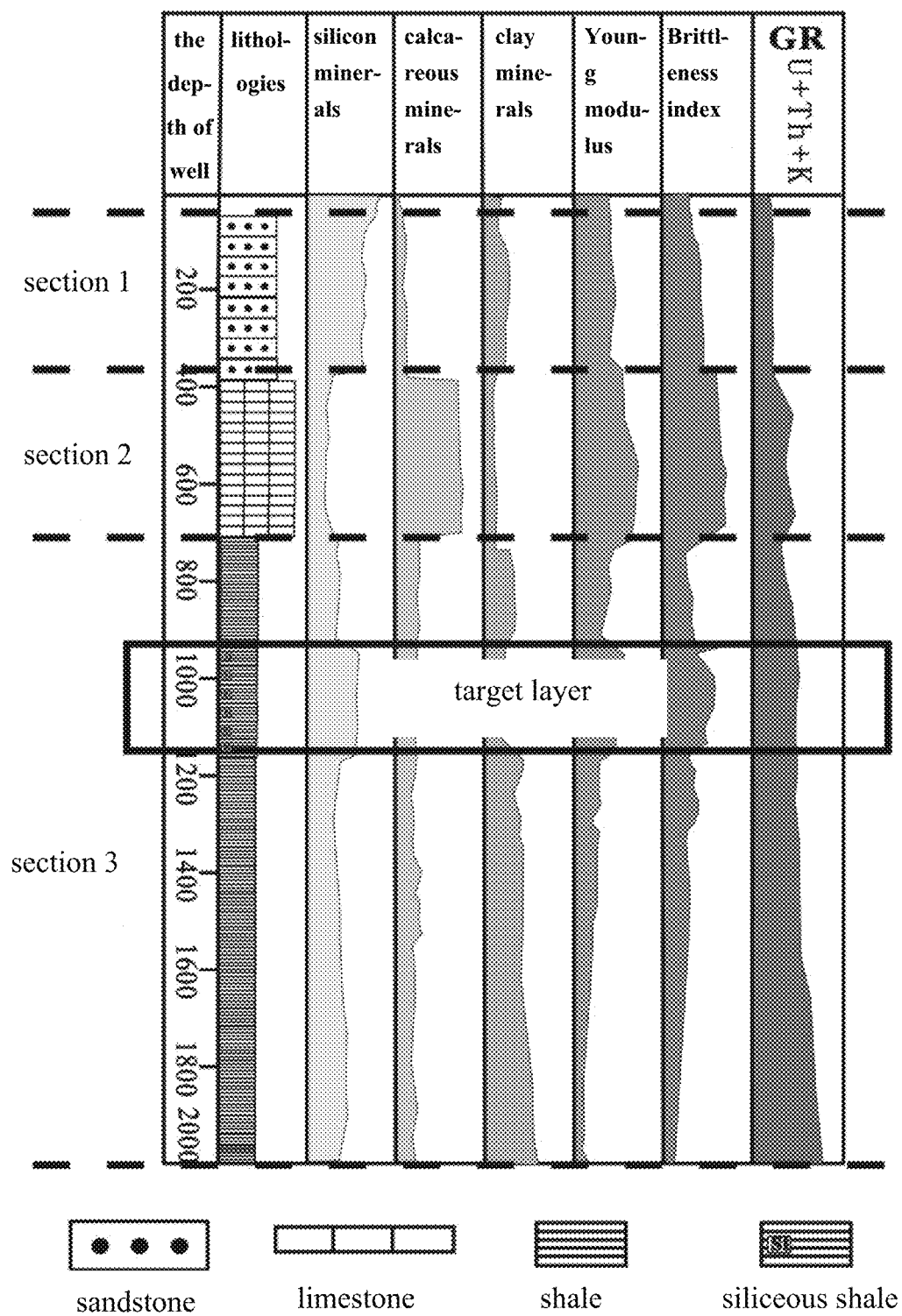
FIG. 7 is a schematic diagram of selecting a target layer of a vertical well for development according to an embodiment of the present disclosure.

As shown in FIG. 7, a siliceous shale layer is selected as the target layer for development in a shale layer of a third section of the vertical well.

Specifically, the assisting of the geosteering of horizontal well drilling and the design of a staged fracturing scheme of horizontal well exploring are illustrated below with reference to FIG. 8:

1) utilizing a drilling system 804 consisting of a drilling rig 801, a drilling pipe 802 and a drilling bit 803 to perform horizontal well drilling on the selected target layer of a vertical well for development, and collecting rock fragments during the horizontal well drilling at equal intervals of a depth of a horizontal well;

2) completing preparation and scanning of scanning samples of rock fragments of the horizontal well, and obtaining data of lithologies, minerals, elements and elastic mechanical parameters corresponding to the depth of the horizontal well by the drilling system 804;

3) drawing the data of lithologies, minerals, elements and elastic mechanical parameters obtained from the vertical well into vertical well pillars 805, and marking the target layer of a vertical well for development;

4) drawing data of lithologies, minerals, elements and elastic mechanical parameters obtained by the horizontal well drilling into horizontal well pillars 806 in real time, comparing the horizontal well pillars with the vertical well pillars, detecting an accurate section of the horizontal well drilling in real time, timely adjusting a direction of horizontal well drilling to ensure accurate drilling of the drill bit at the target layer, thus the geosteering of horizontal well drilling is assisted.

Figure 8:
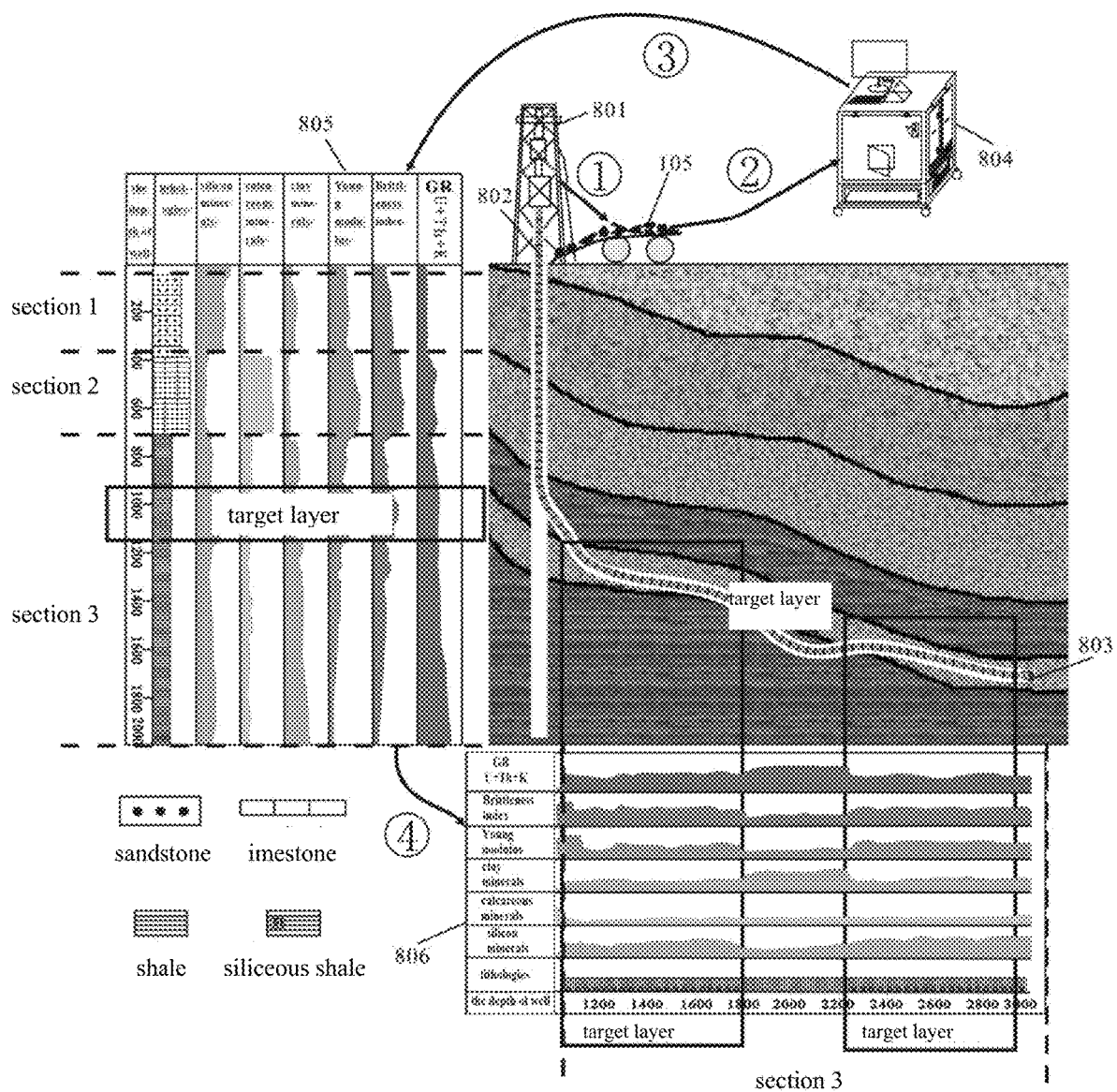
FIG. 8 is a schematic diagram of assisting geosteering of horizontal well drilling and the design of staged fracturing scheme of horizontal well exploring according to an embodiment of the present disclosure.

As shown in FIG. 8, the target layer of the horizontal well drilling is the siliceous shale layer in the third section. When the horizontal well drilling is performed at a depth of 2000 m, it is found that the drilling reached a lower shale layer of the siliceous shale layer by comparison of the horizontal well pillars and the vertical well pillars, thus timely adjusting the drill bit upwards to ensure that the horizontal well drilling is always preceding at the siliceous shale layer, thus the geosteering of horizontal well drilling is achieved. After completion of horizontal well drilling, the horizontal well pillars are able to be used as an important basis for the design of a staged fracturing scheme of horizontal well exploring, such as the design of a staged fracturing scheme of horizontal well exploring for shale gas, thus the accuracy and efficiency of oil and gas exploration can be improved. In addition, the horizontal well pillars are able to be used for calibrating mud logging well pillars and line logging well pillars to improve accuracy of mud logging and line logging.

In a traditional technology, the cost of collecting rock cores is high. Taking a stratum with a length of 1000 m as an example, when a rock core with a length of 1000 m is collected from the stratum, a special sample drilling pipe is used for sampling, at least 50 times of sampling are needs to complete the sampling work. A cost for one sampling is at least 100,000 yuan, therefore, a cost for completing the sampling of whole rock core with a length of 1000 m is at least 5 million yuan. Moreover, the rock core with a length of 1000 m after being collected further need to be transported to a laboratory in a city for analysis according to the prior art. If the cost of preparation and test analysis for one sample is 5,000 yuan, and one sample is analyzed for one meter of the rock core, the whole rock core with a length of 1000 m will need at least 5 million yuan for analysis. In sum, at least 10 million yuan is needed to complete analysis of the rock core with a length of 1000 m using the existing technology, and considering the thickness of a formation is generally more than 3000 m, the collection of rock cores will need more money.

By using the scanning system and the scanning analysis method provided by the present disclosure, the rock fragments that automatically brought to a ground while drilling can be directly collected as rock fragments samples, thus greatly saving the cost of sampling in the traditional methods. And the total cost for analyzing a sample with a length of 1000 m will not exceed 1 million at least 90% of research funding can be saved.

In addition, it takes a long time (at least 2 months) to complete sampling of the rock core with a length of 1000 m, while using the technical solutions provided by the present disclosure, it only needs about 2 weeks for collecting and finishing analyzing of the sample, thus the work efficiency can be greatly improved.

What is claimed is:

1. A system for scanning while-drilling rock fragments in an oil and gas field, comprising a sample preparation mold and a rock fragments scanning apparatus; the sample preparation mold is configured to quickly batch preparing small rock fragments samples generated during a while-drilling process in an oil and gas field into large-area scanning samples, and an acquisition cost of the scanning samples is able to be greatly reduced by using the small rock fragments samples to prepare the scanning samples; the rock fragments scanning apparatus is configured to perform batch scanning and analyzing of the scanning samples in an oil and gas field, and the rock fragments scanning apparatus comprises: a structure configured to fix hardware of the rock fragments scanning apparatus and; a scanning unit configured to perform canning and analyzing of the scanning samples; a control unit configured to control a scanning process of the scanning unit; a housing unit configured to protect internal hardware of the rock fragments scanning apparatus so as to realize quick disassembly and dust prevention, wherein the sample preparation mold comprises a first mold body and a second mold body, side surfaces of the first mold body and the second mold body are provided with a buckle apparatus, and opening and closing the buckle apparatus enables the first mold body and the second mold body to be assembled and disassembled: the first mold body and the second mold body each comprises a plurality of half-holes and when the first mold body and the second mold body are assembled, the half-holes of the first mold body and the half-holes of the second mold body are in one-to-one correspondence to form a plurality of sample preparation holes; a depth of the sample preparation holes is smaller than a height of the sample preparation mold; bottom surfaces of the first mold body and the second mold body comprise positioning hole caps so as to realize assembling and positioning of the first mold body and the second mold body.

2. The system for scanning while-drilling rock fragments in the oil and gas field according to claim 1, wherein the sample preparation mold, which is durable and easy for a resin to cool and dissipate heat and made of stainless steel, enables the small rock fragments samples to be quickly batch prepared into the scanning samples.

3. The system for scanning while-drilling rock fragments in the oil and gas field according to claim 1, wherein a process of preparing small rock fragments samples generated during the while-drilling process in the oil and gas field into the large-area scanning samples by using the sample preparation mold is:

while-drilling rock fragments collecting: collecting the while-drilling rock fragments of a target layer that returned to a ground together with a drilling mud;

while-drilling rock fragments screening and classifying: first using a sieve with large sieve pores to remove the while-drilling rock fragments with large particle size of a non-target layer that may fall from a well wall, and then using a sieve with small sieve pores to remove the while-drilling rock fragments with too small particle size to analyze, the while-drilling rock fragments with a particle size of 40 to 200 meshes are screened as samples to be tested;

washing: washing and drying the samples to be tested; a washing method is determined according to a composition of the drilling mud, and the while-drilling rock fragments of an oil-based drilling mud is washed with an oil displacement agent for several times, then washed with water and dried, and the while-drilling rock fragments of a water-based drilling mud is directly washed with water, then dried, the washed samples thereby are obtained;

resin injection molding: putting the washed samples into the sample preparation holes of the sample preparation mold, then quickly pouring resin ab glues into the sample preparation holes, and quickly stirring the washed samples and the resin ab glues, after standing, the rock fragments of the washed samples and the resin ab glues are cured together, then the scanning samples are prepared;

polishing: polishing the prepared scanning samples with a polishing machine until the scanning fragments have flat surfaces, then polished samples are obtained;

coating conductive layers: coating conductive layers on surfaces of the polished samples.

4. The system for scanning while-drilling rock fragments in the oil and gas field according to claim 1, wherein the structure comprises: a structural skeleton configured to fix and protect hardware devices in the rock fragments scanning apparatus, the structural skeleton is made of a stainless steel material, and comprises three horizontally arranged plate-like structures and a plurality of vertically arranged columnar structures connected to the plate-like structures, and the structural skeleton is a rectangular skeleton structure comprising an upper structure and a lower structure; a locking caster disposed on a bottom of the structural skeleton for moving the rock fragments scanning apparatus; a sliding rail drawer disposed in the lower structure of the structural skeleton; the anti-vibration sub-unit disposed on a bottom of the sliding rail drawer for reducing the influence of drilling vibration in a drilling site on the quality of a scanned image; the temperature control sub-unit disposed on the upper structure and the lower structure of the structural skeleton, is composed of a plurality of fans and used for dissipating heat generated by the rock fragments scanning apparatus outside so as to improve adaptability of the rock fragments scanning apparatus to a high temperature environment of a wild desert, and ensure normal operation of the hardware devices.

5. The system for scanning while-drilling rock fragments in the oil and gas field according to claim 4, wherein the scanning unit comprises:

a scanning and detecting system chamber disposed in the upper structure of the structural skeleton for maintaining a vacuum environment, and a backscattering electron probe, a secondary electron probe, a EDS spectrum probe, and a sample table are disposed inside the scanning and detecting system chamber; wherein the backscattered electron probe is configured to collect a backscattered electron signal, the secondary electron probe is configured to collect a secondary electronic signal, the EDS spectrum probe is configured to collect an x-ray signal, and the sample table is a full-automatic motor sample table capable of loading a plurality of samples;

an electron gun and a lens barrel, wherein the electron gun is configured to provide a high-energy focused electron beam, and disposed on a top of the upper structure of the structural skeleton; one end of the lens barrel is accommodated in the scanning and detecting system chamber for focusing the electron beam and aligning the focused electron beam to the sample table;

a vacuum pump configured to achieve evacuation of the scanning and detecting system chamber.

6. The system for scanning while-drilling rock fragments in the oil and gas field according to claim 4, wherein the control unit comprises:

a scanning control subunit configured to control the electron gun, the lens barrel, the backscattered electron probe, the secondary electron probe, the EDS spectrum probe, and the sample table, and disposed on a side surface of the upper structure of the structural skeleton, wherein the scanning control subunit is of plate-like structure, a 90 degree connector is provided at a bottom of the plate-like structure of the scanning control subunit for pulling the scanning control subunit with a plate-like structure from a vertical state to a horizontal state so as to facilitate inspection and maintenance of the scanning control subunit;

a software control subunit configured to implement control of all software and hardware, data storage and transmission, and disposed in the sliding rail drawer;

an input subunit through which an operator is able to set scan parameters;

a display subunit configured to display a scanning result.

7. The system for scanning while-drilling rock fragments in the oil and gas field according to claim 4, wherein the housing unit comprises:

a housing panel and a frame, the housing panel is a main package sub-unit of the housing unit, and is of a double-layer structure, and is made of an aluminum alloy material, and the housing panel and the frame are used together to realize quick disassembly and assembly;

buckles and block grooves disposed on the housing panel and the frame, and the buckles and the block grooves are used together to make portions of the housing unit to be mutually connected and the housing unit is fixed on the structural skeleton;

a dust prevention sub-unit configured for preventing dust, and comprising a dust prevention filter, and disposed at a position corresponding to the temperature control sub-unit, and the dust prevention sub-unit is able to be used as a heat dissipation passage of the temperature control sub-unit;

a sample chamber cover for loading and unloading a sample, a power switch cover for protecting a switch button, an electron gun cover for replacing an electron gun filament, and a software control subunit cover for shielding the software control subunit; all covers are disposed on the housing panel, and have buckles capable of being rotatably opened and closed.

8. A method for scanning and analyzing while-drilling rock fragments in an oil and gas field, using the system for scanning the while-drilling rock fragments in the oil and gas field according to claim 1, wherein the method comprises a scanning step and an analysis step;

the scanning step is configured to perform scanning by using the system for scanning the while-drilling rock fragments in the oil and gas field to complete batch scanning tests of the scanning samples of rock fragments, and obtain scanning test results of the scanning samples;

the analysis step comprises an elastic mechanical parameters calculation substep and an oil and gas field application substep;

in the elastic mechanical parameters calculation substep, the elastic mechanical parameters is calculated by using the scanning test results of the scanning samples;

in the oil and gas field application substep, a target layer of a vertical well for development is selected by the system; and geosteering of horizontal well drilling and design of a staged fracturing scheme of horizontal well exploring are assisted by the system, the scanning step completes a centimeter-scale large visual field scanning of a sample by separately scanning each subarea, and the scanning step in turn comprises:

loading the scanning samples, setting a scanning area of one scanning sample, selecting a subarea for scanning, obtaining a backscattered electron image of the subarea by using the backscattering electron probe, obtaining a secondary electron image of the subarea by using the secondary electron probe, removing a non-rock fragment visual field in the subarea, obtaining X-ray information of the subarea by using the EDS spectrum probe, automatically identifying and quantitatively analyzing elements in the subarea, automatically identifying and quantitatively analyzing minerals in the subarea by using a mineral database and obtaining a mineral image of the subarea, selecting a next subarea for scanning, after completing scanning of all subareas, automatically identifying lithologies of the scanning sample by using a lithologies database, turning to a next scanning sample for scanning, after completing scanning of all scanning samples, reloading a new batch of scanning samples for scanning.

9. The method for scanning and analyzing while-drilling rock fragments in an oil and gas field according to claim 8, wherein the elastic mechanical parameters calculation substep is:

mosaicking backscattered electron images, secondary electron images and mineral images of a series of subareas together by an image mosaic software to obtain a backscattered electron image, a secondary electron image and a mineral image of a centimeter-scale large visual field;

quantitatively analyzing a surface structure of the scanning sample by using the backscattered electron image of the centimeter-scale large visual field or the secondary electron image of the centimeter-scale large visual field to obtain surface structure quantitative analysis data;

quantitatively analyzing minerals contents of the scanning sample by using the mineral image of the centimeter-scale large visual field to obtain mineral quantitative analysis data;

calculating the elastic mechanical parameters according to an equivalent medium model in combination with the surface structure quantitative analysis data and the mineral quantitative analysis data.

10. The method for scanning and analyzing while-drilling rock fragments in an oil and gas field according to claim 8, wherein the target layer of a vertical well for development is selected by the system comprising:

sampling the rock fragments of a vertical well of a certain block at equal intervals of a depth of the vertical well, completing preparation and scanning of the scanning samples of rock fragments to obtain data of lithologies, minerals, elements and elastic mechanical parameters corresponding to the depth of the vertical well;

drawing the obtained data of lithologies, minerals, elements and elastic mechanical parameters into vertical well pillars corresponding to the depth of the vertical well;

dividing the vertical well pillars into different sections according to different trend of the data of lithologies, minerals, elements and elastic mechanical parameters corresponding to the depth of the vertical well;

analyzing the different sections of the vertical well pillars to determine the target layer for development.

11. The method for scanning and analyzing while-drilling rock fragments in an oil and gas field according to claim 8, wherein the geosteering of horizontal well drilling and design of a staged fracturing scheme of horizontal well exploring are assisted by the system comprising:

utilizing a drilling system to perform horizontal well drilling on the selected target layer of a vertical well for development, and collecting rock fragments during the horizontal well drilling at equal intervals of a depth of a horizontal well;

completing preparation and scanning of scanning samples of rock fragments of the horizontal well, and obtaining data of lithologies, minerals, elements and elastic mechanical parameters corresponding to the depth of the horizontal well;

drawing the data of lithologies, minerals, elements and elastic mechanical parameters obtained from the vertical well into vertical well pillars, and marking the target layer of a vertical well for development;

drawing data of lithologies, minerals, elements and elastic mechanical parameters obtained by the horizontal well drilling into horizontal well pillars in real time, comparing the horizontal well pillars with the vertical well pillars, detecting an accurate section of the horizontal well drilling in real time, timely adjusting a direction of horizontal well drilling to ensure accurate drilling of the drill bit at the target layer, thus the geosteering of horizontal well drilling is assisted;

after completion of the horizontal well drilling, the horizontal well pillars are able to be used as an important basis for the design of a staged fracturing scheme of horizontal well drilling; the horizontal well pillars are able to be used for staged fracturing scheme development of horizontal well exploring of shale gas so as to improve accuracy and profits of oil and gas exploration, and the horizontal well pillars are able to be used for calibrating mud logging well pillars and line logging well pillars so as to improve accuracy of mud logging and line logging.

* * * * *